(12) United States Patent
Watson et al.

(10) Patent No.: US 7,418,881 B2
(45) Date of Patent: Sep. 2, 2008

(54) DILUTION SYSTEM AND METHOD

(75) Inventors: David John Watson, Hanley Swan (GB); Lewis Meurig Jones, West Malvern (GB); James Franklin Kovach, Malvern (GB)

(73) Assignee: Malvern Instruments Limited, Malvern (GB)

( * ) Notice: Subject to any disclaimer, the term of this patent is extended or adjusted under 35 U.S.C. 154(b) by 0 days.

(21) Appl. No.: 10/545,820

(22) PCT Filed: Feb. 16, 2004

(86) PCT No.: PCT/GB2004/000599

§ 371 (c)(1), (2), (4) Date: Nov. 28, 2006

(87) PCT Pub. No.: WO2004/072603

PCT Pub. Date: Aug. 26, 2004

(65) Prior Publication Data

US 2007/0137314 A1 Jun. 21, 2007

(30) Foreign Application Priority Data

Feb. 14, 2003 (GB) ................................ 0303470.9

(51) Int. Cl.
*G01N 15/00* (2006.01)
(52) U.S. Cl. .................................... 73/865.5
(58) Field of Classification Search ........................ None
See application file for complete search history.

(56) References Cited

U.S. PATENT DOCUMENTS 4,634,560 A 1/1987 Eckert
5,054,309 A * 10/1991 Mettes et al. ................. 73/1.03
5,090,258 A * 2/1992 Yamasaki et al. ........ 73/863.03
5,109,708 A 5/1992 Lawless
5,454,912 A 10/1995 Dougherty
5,676,494 A 10/1997 Ruch
5,895,869 A 4/1999 Von Behrens et al.
5,907,108 A 5/1999 Garcia-Rubio et al.
6,286,376 B1 9/2001 Davidson et al.
6,383,462 B1 5/2002 Lang
6,416,642 B1 7/2002 Alajoki et al.
7,100,459 B2 * 9/2006 Gehner et al. ............ 73/863.03

FOREIGN PATENT DOCUMENTS

EP 0911296 4/1999
GB 2028164 A 3/1980

* cited by examiner

*Primary Examiner*—Robert R Raevis
(74) *Attorney, Agent, or Firm*—Baker Botts L.L.P.

(57) ABSTRACT

A multi-stage dilution device, comprising a first stage dilution apparatus (A), and a second stage dilution apparatus (B), each of the stage dilution device comprising:—(i) a housing (1) having a diluent inlet (7); (ii) a sample inlet (2) having a sample introducer within the housing (1) adapted to introduce the sample at an introducer point (4) within the housing (1); and, (iii) a mixing conduit (5) mounted at least partially within the housing (1), the mixing conduit (5) having an inlet section comprising a mouth (10), and a fluid outlet (8), and a throat section (9) capable of producing a pressure drop within the mixing conduit (5), the pressure drop being sufficient to draw sample through the sample inlet (2); the introducer point (4) of the sample inlet (2) being proximate the mixing conduit inlet; and wherein the fluid output (8) of the first stage dilution apparatus (A) is in communication with the sample inlet (2) of the second stage dilution apparatus (B). A method of diluting a sample is also disclosed.

32 Claims, 11 Drawing Sheets

DILUTION SYSTEM AND METHOD

CROSS-REFERENCE TO RELATED APPLICATIONS

This application is a national phase of International Application No. PCT/GB2004/000599, filed Feb. 16, 2004, published Aug. 26, 2004, and entitled "Dilution System And Method," which claims priority from Great Britain Application No. 0303470.9, filed Feb. 14, 2003, both of which are incorporated by reference in their entireties herein, and from which priority is claimed.

FIELD OF INVENTION

The present invention relates to improvements in or relating to the sampling of a mixture containing particles to be analysed, for example, for particle characterisation, and to sampling apparatus therefor.

BACKGROUND OF THE INVENTION

Analytical measurements of particle dispersions frequently require dilution in order to eliminate particle-particle interactions as an element in the analysis. For example, in light scattering measurements, it is desirable to operate in the regime in which single-particle scattering approximations are valid. It is also desirable to operate within the linear range of the analytic instrumentation, typically at concentrations in the order of milligrams of particulates per gram of diluent, for performing static and dynamic light scattering spectroscopy and particle counting. If a sample is too concentrated, some analysers will not work properly.

The method of Ultrasound Spectroscopy has been recently developed for particle characterisation because it demonstrates linearity of the attenuation spectrum to higher concentrations than light scattering. Nevertheless the concentrations achieved are still not high enough for all slurries to be measured in-line and thus some dilution is often desirable or essential.

The corrections for particle-particle interactions involve approximations of complex real particle behaviours and thus an imperfect correction. Thus there remains an advantage for dilution even where particle-particle corrections are available, since it avoids the need for introducing these approximations.

Methods for the characterisation of dispersions containing, for example, micrometer and submicrometer-size particles, are important in understanding particulate systems in general. While detection systems have been disclosed for performing measurements on such dispersions, the sampling problem remains to be addressed effectively. A number of disadvantages exist in the prior art methods and apparatus. For example, difficulties have been observed in obtaining representative samples. Additionally mixing times of the sample and diluent in order to ensure uniform distribution of the sample throughout the diluent, and the time required for the measurement tend to be large and consequently the sampling and measuring process can be unwieldy and inefficient.

A further problem observed with the prior art is that often an entire sample is diluted and fed through an analyser. This type of batch analysis results in a substantial amount of diluent being required and accordingly, a large reservoir volume in which a homogenised dispersion of particles in diluent takes place.

U.S. Pat. No. 5,907,108 (hereinafter referenced as '108) discloses a system and method for sampling and dilution of homogenous particle dispersions. Sample and diluent are combined by a metering process in which the dilution ratio is controlled by the relative flow rates as determined by pumps. The combined sample and diluent are mixed by the use of a mixing conduit where the sample is extruded by the pump into a passing stream of diluent, also pumped. The mixing of sample with the dispersant occurs slowly in a conduit which requires stirring aids such as baffles to achieve full mixing. The dilution ratio of a single stage is limited only by the metering ability of the pumps.

The dilution is further increased by resampling the output of one dilutor with another, the $2^{nd}$ and subsequent stages all having their dilution ratios each controlled by the flow rates of pumps. At least two pumps, or pump heads, are required per stage of dilution. Further, in the '108 patent exemplification the flow rates of sample are relatively very low and residence times within the dilutor very high, for example, typically on the order of a minute. Additionally, the '108 patent exemplification design is very difficult to clean or unblock. This may only be achieved by automatic sequence control of the various pumps with its associated complexity.

SUMMARY OF INVENTION

In accordance with a first aspect of the present invention there is provided a dilution apparatus comprising:
(i) a housing having a diluent inlet;
(ii) a sample inlet having a sample introducer within the housing; and,
(iii) a mixing conduit mounted at least partially within the housing, the mixing conduit having an inlet section comprising a mouth, and a fluid outlet;

characterised in that the introducer of the sample inlet is proximate the mixing conduit inlet, the mixing conduit having a throat section capable of producing a pressure drop within the mixing conduit, the pressure drop being sufficient to draw sample through the sample inlet.

In accordance with the second aspect of the present invention there is provided a dilution apparatus comprising:
(i) a housing having a diluent inlet;
(ii) a mixing conduit mounted at least partially within the housing, said mixing conduit having a throat section, an inlet section comprising a mouth, and a fluid outlet; and,
(iii) a sample inlet capable of introducing sample proximate the mixing conduit inlet;

characterised in that the mixing conduit inlet section is remote to the diluent inlet.

In accordance with a further aspect of the present invention, there is provided a dilution apparatus comprising a mixing conduit having an elongate extent and a mouth at an inlet end, said mouth comprising a diluent inlet adapted to accept diluent during use; and a sample introducer having an inlet disposed in the region of the mouth and spaced from the mixing conduit so as to provide said diluent inlet between said sample outlet and said mouth, the position of the inlet of the sample introducer relative to the mouth of said mixing conduit being arranged to cause sample to be drawn out of the sample introducer by the flow of diluent entering the mouth, past the sample introducer inlet.

Such apparatus' typically do not require this use of positive displacement purposes to introduce sample into the apparatus', or can use a single pump to pump diluent into the apparatus' This results. in a simplification of construction over current systems and also reduces the need for electrical apparatus, pumps, to be located near potentially flammable diluents thereby increasing the safety of the apparatus over current systems.

In accordance with a further aspect of the present invention, there is provided a method of diluting a sample, comprising entraining a sample from a sample inlet by providing a flow of diluent in the elongate direction of the outlet, past the end of the sample inlet, into a mixing channel, sample being drawn out of the sample inlet due to the flow of diluent.

In accordance with a further aspect of the present invention, there is provided a method of diluting a particle sample prior to analysis of the particles in the sample, comprising entraining an amount of sample in a diluent within a dilution apparatus, said dilution apparatus comprising a diluent inlet, a sample inlet, a fluid outlet and a mixing conduit, the dilution ratio being determined by the dimensions and proximity of the sample inlet and the mixing conduit for a given flow rate of diluent.

In a further aspect of the present invention, there is provided a method of cleaning and/or unblocking a dilution apparatus as defined above, comprising closing the fluid outlet of the dilution apparatus whilst applying fluid pressure to the apparatus via the diluent inlet, thus causing venting of fluid through the sample inlet. Thus, to remove a blockage, fluid may be caused to flow in the mixing conduit in the opposite direction to normal.

In a further aspect of the present invention, there is provided a sampling system adapted to dilute a plurality of samples to undergo analysis, comprising:
  (i) a multiple sample presentation means;
  (ii) a dilution apparatus, as defined herein;
  (iii) means to bring the sample inlet into fluid communication with one or more samples; and,
  (iv) optionally computer processing means to control the system.

According to a further aspect of the present invention there is provided a method of sampling a plurality of samples to undergo analysis, comprising the steps of:
  (i) providing a plurality of discrete samples;
  (ii) bringing a sample inlet into contact with one or more of the samples; and,
  (iii) removing and diluting a succession of samples from one or more of the plurality of samples in a dilution apparatus, as defined herein.

Further, according to another aspect of the present invention, there is provided an automatic sample preparation device having an outlet adapted for coupling to a particle characteristic analyser; a sample extraction station; a sample vessel vehicle adapted to bring a plurality of sample vessels in turn to said sample extraction station; a sample extractor provided at the sample extraction station adapted to extract samples from the sample vessels as they are brought in turn to the sample extraction station; and, a sample dilutor adapted to receive samples from the sample extractor and dilute them prior to passing diluted samples to the outlet, the improvement comprising having a combined sample extractor and dilutor.

In one aspect, the present invention differs from the prior art in that the sampling is achieved by the action of the flow of diluent under pressure with a dilution ratio that is approximately fixed by the geometry of the dilutor and not user variable. The dilutor is thus powered by the dispersant pressure only and sample is entrained hydrodynamically providing a no moving parts sampler that has substantial technical advantages for long term reliability and intrinsically safe operation. No pumps are required for the dilutor, an advantage that increases the more stages of dilution are required.

The current invention requires a significant flow rate in order to create the hydrodynamic entrainment of the sample. This allows the use of turbulent flow only to provide homogenous mixing of sample within the mixing conduit. It also means that the residence time for sample within the device is very short, typically a few seconds. Metering of sample is continuous into the sampler and thus the measuring apparatus receives diluted sample at all times that is near time synchronous to the process condition.

The current design allows for a convenient construction of stacked dilutors as described below to create a multi-stage dilutor that achieves higher dilutions. Each dilutor may be a unit design that can be assembled in stages.

The current design also allows a simple and convenient means for obtaining a clean background and for cleaning the probe tip by means of temporarily blocking ports whilst the probe remains pressurised and drawing diluent.

The apparatus of the present invention is preferably coupled remotely or formed integrally with a particle characteristic analyser, preferably of conventional type.

The apparatus of the present invention may be used in the continuous monitoring of a process in which particulates are involved and their characteristics are a control or monitoring objective. In fact, the present apparatus may be used to continuously monitor a process by continuously, or frequently, removing a sample from a process, and diluting the sample for analysis. Thus, the particle characteristic may be monitored continuously throughout the active processing of the raw slurry. Since the residence time in the dilutor is very short, for example, a few seconds, the sample measured by the analyser is virtually synchronous to the process being sampled allowing near instantaneous detection of change.

The apparatus is adapted to run with a liquid diluent, for example water. Preferably, the apparatus is adapted to receive pressurised diluent. It should be understood that alternative diluents may be used. Alternative diluents may be used where, for example, the diluent is not compatible with the sample, or the analyser is run using a diluent in the analysis cell which is incompatible with the dilutor diluent or sample. A diluent flow passage may be provided to supply diluent to the diluent inlet. The flow passage may be a tube or a connection chamber such as a manifold port.

Preferably, the dilution apparatus of the present invention comprises no moving parts and is driven simply by diluent pressure or by a phenomenon caused by the application of diluent pressure, for example, the venturi effect. The dilution apparatus of the present invention is preferably pumpless.

Preferably, the apparatus of the present invention is used to dilute samples to be used in analysis of the samples particle size distribution.

The dilution apparatus housing is preferably substantially cylindrical, most preferably circularly cylindrical. More preferably, the housing comprises an elongate tube. The housing preferably comprises an outer sheath having a cavity into which diluent is forced through the diluent inlet. The diluent inlet is preferably located proximate to one end of the cavity. Preferably the cavity has a length in the range of 10 mm-1000 mm, more preferably 25 mm-200 mm, most preferably 40 mm-100 mm. The cavity preferably has a diameter of 5 mm-100 mm, more preferably, 7 mm-50 mm, most preferably 9 mm-20 mm.

The housing preferably has surfaces proximate the mixing conduit inlet, adapted to direct the diluent towards the mouth. Preferably, the surfaces are curved. More preferably, the surfaces are adapted to converge and/or reverse the flow of fluid moving from the diluent inlet towards the diluent inlet of the mixing conduit. In a preferred embodiment, these surfaces cause flow of the diluent past the sample inlet introducer, towards the mouth of the mixing conduit.

Preferably the mixing conduit comprises a substantially cylindrical tube. Preferably the mixing conduit is mounted within the housing and has an inlet section at a first end. This first end is preferably remote to the diluent inlet and proximate to the sample inlet. Preferably, the mixing conduit's longitudinal axis is substantially parallel with the longitudinal axis of the housing. Preferably, the mixing conduit is substantially co-axial with the housing. Preferably both the sample inlet and the mixing conduit inlet section are located proximate an end of the housing remote from the diluent inlet.

Preferably either or both of the sample inlet and the mixing conduit inlet section are located at least 30 mm from the diluent inlet, preferably at least 40 mm, most preferably at least 50 mm.

The mixing conduit preferably comprises a substantially cylindrical tube having a throat section. Preferably, the throat section is proximate the mixing tube inlet section, hereinafter referred to as the mouth, and is capable of creating a pressure drop within the mixing conduit. Preferably, the mouth comprises a surface that converges to the throat section in the direction of fluid flow through the mixing conduit. In this embodiment, the throat section has a narrower cross-section than the mouth. The converging mouth is preferably co-axial with the longitudinal axis of the mixing conduit. Furthermore, the mouth and throat sections are preferably circularly symmetrical about the axis of the mixing conduit. Preferably the shape of the mixing conduit between the mouth and the throat of the mixing tube is either a smooth converging surface or a curved parabolic surface. In a particularly preferred embodiment, the shape of the mixing conduit between the mouth and throat is approximately frustoconical.

Preferably the mixing conduit has a length in the range of 10 mm-1000 mm, more preferably 35 mm-200 mm, most preferably 50 mm-100 mm. Preferably the mixing conduit inlet has an internal diameter in the range of 3 mm-20 mm, more preferably 5 mm-12 mm, most preferably 7 mm-10 mm. Preferably the throat section of the mixing conduit has an internal diameter in the range of 0.5 mm-10 mm, more preferably 1 mm-5 mm, most preferably 2 mm-4 mm, in particular 3 mm.

The throat section is preferably succeeded by a portion of the mixing conduit having a greater cross-section or diameter, so as to create a venturi effect within the mixing tube, thus causing adequate mixing of diluent with sample. The throat section is preferably succeeded by a diverging surface in the direction of fluid flow that opens out into this portion of the mixing conduit. This section is hereinafter referred to as the pressure drop section. This section is preferably approximately frustoconical in shape.

The throat section may be formed by the juncture of the converging mouth section and the diverging pressure drop section. Thus, the throat section may comprise a discrete annular ridge. Alternatively, there may be a tubular section connecting the converging mouth and diverging pressure drop sections. Finally the transition from the throat section to the diverging pressure drop section may be a continuous section whose shape is optimised to maximise the pressure drop experienced at the introducer tip.

Succeeding the diverging pressure drop section in the diluent flow direction, the mixing conduit may comprise a substantially parallel walled tubular section leading to the diluent outlet. This section is preferably cylindrical in radial cross-section.

The sample inlet is preferably an elongate member, preferably a cylindrical tube that is capable of being dipped in, or otherwise brought into fluid contact with, a sample to be analysed. Preferably, the sample inlet comprises a lumen, preferably a cylindrical lumen. Preferably, the sample inlet is disposed substantially parallel to the elongate axis of the mixing conduit, most preferably co-axial therewith. Preferably, the sample inlet is substantially co-axial with the mixing conduit. One end of the sample inlet is preferably capable of contacting a sample and transmitting it to the introducer, discussed immediately below. A second end of the sample inlet is preferably located within the housing, preferably proximate the mouth of the mixing conduit. This end is hereinafter referred to as the sample inlet introducer. This end introduces sample into the dilution apparatus.

Preferably, the sample inlet tube is of a smaller diameter than the narrowest diameter of the mixing conduit. The sample inlet tube preferably has an internal diameter in the range of 1-4 mm, more preferably 1.2-2 mm most preferably 1.3-1.5 mm. The sample inlet introducer is preferably of a complementary shape to the mouth of the mixing conduit, most preferably frustoconical. Preferably, the sample inlet introducer tip extends in the elongate direction, at least to the mouth of the mixing conduit.

The separation of the introducer and the mouth may be in the range of 0.5 mm-5 mm, more preferably 0.75 mm-3 mm, most preferably 1 mm-2.5 mm. In a preferred embodiment, the sample inlet introducer extends into the mouth of the mixing conduit, preferably recessed within the mouth. Preferably, the separation of the introducer and the mouth is adapted so that the entrainment ratio of sample to diluent flow rates is a maximum.

Preferably the sample inlet has a tapering extension surface which converges along its elongate length. Preferably, there is a diluent flow gap defined between the extension surface of the sample inlet and the mouth of the mixing conduit. Preferably, the diluent flow gap is generally annular at a cross-section taken normal to the elongate axis, the tapering external surface of the inlet proximate the tapering interior surface of the mouth, being generally co-axial.

It is particularly preferred that the sample inlet introducer is in direct contact with the diluent and/or sample when the apparatus is in use. In other words, the sample inlet does not merely drip sample into the housing cavity; sample is drawn substantially continuously through the introducer tip by the pressure drop caused by the venturi effect in the mixing conduit. The position of the sample inlet opening is important as the venturi effect actively draws diluent and sample into the mixing conduit. Thus, if intimate contact is not maintained with the diluent, consistent entrainment of sample may not be achieved.

Preferably, there is a diluent flow gap between the introducer and the surface of the mouth of the mixing conduit.

Preferably the sample inlet lumen diameter is greater than three times the largest particle size expected in the sample. A diameter of less than 3 times the expected particle size can lead to blockage of the tube. Therefore, for example, a 1.5 mm diameter sample inlet tube represents the smallest preferred diameter for a system handling particles up to 500 micrometers.

The sample inlet may be made adjustable, such that the separation of the introducer tip from the mixing tube may be adjusted. For example, a manually releasable and lockable position lock may be provided, such as a collet lock. This may be employed so that the actual dilution rate can be fine tuned up or down, typically being pre-set by a supplier before a user receives the apparatus.

In use, the apparatus preferably has a fixed geometry. That is to say that subsequent to initial tuning and calibration of the apparatus, the apparatus is preferably run without adjustment of any of its constituent parts.

It is evident that the present invention may be used to sample bulk or discrete samples, and to do so in a continuous fashion. It is thus important that the sample inlet is adapted to be able to sufficiently contact and uptake sample. The pressure drop caused by the venturi effect should be sufficient to suck sample through the sample inlet into the apparatus. This is particularly useful in the hand-held embodiments of the invention, described below, as the device may be manually positioned in any desired zone of a sample reservoir, stream etc., and sample may be easily withdrawn. Extensions, such as flexible tubing may be applied to the sample inlet to facilitate uptake of sample.

In use, the diluent passes through the diluent inlet into the housing. The diluent passes down the cavity of the housing, which preferably has a substantially circularly symmetric cross-section, towards the mixing conduit inlet. The diluent then enters the mixing conduit inlet and passes through the constricted throat section that creates a pressure drop. The pressure drop causes entrainment of the sample from the sample inlet.

The sample is then mixed with the passing diluent continuously and the turbulent flow conditions created within the mixing conduit ensures that the initial core of sample is rapidly intermixed with the diluent annulus surrounding it. The advantage of using a housing and the mixing tube, mounted therein, preferably co-axially therein, and having the diluent inlet remote from the mixing tube inlet, is that an annulus of diluent is forced into the housing cavity, and when reaching the end of the cavity remote the diluent inlet, is converged into the mixing conduit inlet and past the sample inlet, the diluent converging on the sample from all sides. This creates a better mixing of the sample and a more consistent draw of sample from the sample inlet. The diluted sample so formed may then be taken directly to an analyser, for example, a laser diffraction particle sizing instrument, and then disposed of.

Alternatively, in a particularly preferred embodiment, the sample entrained diluent may pass out of the fluid outlet of a first probe to a second or further dilution apparatus. Hereinafter each dilution apparatus may be referred to as a probe. In this latter embodiment, two or more probes may be coupled together, the fluid outlet of one forming, or being proximate, the sample inlet of another. In this regard, a bridge section may be provided which enables the fluid exit end of one probe to be coupled to a second probe. Such a bridge section preferably comprises engagement means that may enable adjustment of the position and/or separation of one probe from another. The bridge section may also comprise a cavity and a fluid outlet, both of which are in fluid contact with the fluid outlet of a previous probe. The bridge section is preferably assembled co-axially with one or more probes. The volume of the cavity of the bridge section is preferably less that that of the probe. This is important such that the size of the apparatus may be minimised. The bridge section may be a separate apparatus or may be formed integrally with one or more probes.

Accordingly, a series or stack of probes may be coupled, preferably co-axially, to create a predetermined dilution ratio that is approximately a product of the combination of the dilution ratios obtained from each of the probes. Any number of probes in series may be constructed in order to provide the desired dilution ratio. For example 2 to 10 probes are preferred, more preferably, 2-5, most preferably 3, 4 or 5 probes in series.

The second or subsequent probe in a series of connected probes preferably has a sample inlet adapted to extract a volume of the fluid from the preceding probe(s) in such a way that all particles in the fluid are equally likely to be sampled. Fine particles follow the flow faithfully and essentially behave as the fluid does. Larger and denser particles have inertia and follow more ballistic trajectories as well as having a tendency to sediment to the bottom of pipes and containers. One optimum sampling condition is when the velocity of sample in the sample inlet is identical to that of the fluid outlet. This is referred to as the iso-kinetic sampling condition. Another sampling condition is to ensure turbulent mixing conditions within the mixing conduit so that strong fluid recirculation ensures the redistribution of the larger particles. Size related bias in the sampler directly affects the analyser results, most particularly when the characteristic measured is the size distribution. The bias factor $\beta(a)$ can be represented as a ratio of the relative volume of a particular size (a) in the mixing conduit to that in the sampling tip. Clearly the factor $\beta(a)$ would ideally be unity for all (a). In reality this is easily achieved for small sizes and becomes more difficult as the size and particle density increases. The bias factor may be greater or less than 1, some sampling configurations oversample the large particle population whilst others may undersample. An optimum design for the sampling configuration occurs when the achieved bias factor remains effectively unity to the highest size and density limits.

Stacking dilutors exaggerates the effects of bias since they have a multiplicative effect. The bias factor for a stack of probes is the product of the individual bias factors for the size concerned. For this reason an optimum design preferably uses the least number of stacked probes to achieve the necessary dilution.

One advantage of stacking substantially identical dilutors is that it is possible to match the velocities in the fluid outlet to those of the sample inlet by control of the bore of the fluid outlet and sample inlet. In addition because the entrainment ratio is preferably close to constant over a wide range of diluent flow rates this optimisation remains robust against flow rate changes.

The optimum flow rate is one that ensures measurement of a representative sample. Further, there should be sufficient flow to drive the probe(s) reliably, that is generate sufficient pressure drop to make the entrainment stable. Additionally, the probes should preferably achieve the overall dilution ratio that bridges the concentration gap between sample and analyser. Generally it is desirable to consume the minimum of dilution liquid since this is usually added back to the process and could therefore have some impact on the process, or the dispersant needs responsible disposal.

The apparatus may be activated continuously and in a preferred embodiment consumes 0.5-20, more preferably 0.75-10, most preferably 1-3 litres of diluent per minute. The flow rate is most preferably greater than 1 litre/minute. These flow rates preferably represent optimum entrainment of sample.

In a preferred embodiment, each probe is operated at its maximum entrainment rate, even though this means that the dilution ratio is at its lowest. This is because in this operating mode, the probe is at its most robust and is affected least by variations in the environment. The preferred dilution ratio for a single probe is preferably in the range of 5:1-100:1, more preferably 7:1-20:1, most preferably 9:1-15:1, especially about 7, 8 or 9 to one.

The sample is preferably diluted and moved to the particle analysis zone preferably within 1 minute of activation of the apparatus, more preferably within 20 seconds, more preferably still within 10 seconds, most preferably within 1-2 seconds. This results in a very short time for aggregation to occur through dilution shock. It is therefore expected that the impact of dilution on slurries is reduced and that measurements will remain representative of the concentrated state. This also has the advantage of enabling continuous and ongoing analysis of a process.

In a particularly preferred embodiment, the apparatus is configured in an extended cylinder, for example like the "gun" of a pressure washer that may be hand-held. This has the advantage of mobility and ease of use, a user being able to direct the sample inlet into a desired region of sample in order to take a measurement. In this embodiment, a pressure valve may be fashioned into a pistol grip. In the sampling, the trigger depression releases the diluent flow, which is maintained for the duration the trigger is depressed. The diluent begins to entrain sample from the time the dilutor cavities fill and the venturi effect starts. A simple delayed measurement start allows time for material to flow to the analysis cell. The trigger release can stop measurement so that measurement duration is controlled by the length of time the trigger is depressed.

The dimensions of the apparatus according to the present invention must be carefully designed since any significant back-pressure would stall the entrainment of sample. This is attributable to the fact that water is incompressible and therefore any back-pressure in the mixing conduit is directly coupled back to the sample inlet. If the pressure head exceeds the pressure drop caused by the venturi effect, the system will start to pump diluent out of the sample inlet into the sample.

Preferably, the dilution ratio in any fixed geometry of the apparatus will be fixed and controlled by the relative pressure drop at the throat.

Some of the advantages associated with the present invention are that the apparatus is capable of continuous monitoring of a process in which particulates are involved and their properties, such as size, are a control or monitoring objective. The apparatus can be activated continuously and will continuously consume diluent at a rate described above. This diluent and any entrained sample therein may be dumped back into the process downstream of the measurement point. A further advantage is that the entire apparatus is powered by water pressure and all moving parts may be minimised or eliminated all together. Further, the internal parts of the apparatus are continually flushed with clean dispersant or diluted slurry in normal operation and therefore maintenance is minimised.

Background measurements are easily obtained. The sample inlet may simply be brought into contact with background diluent, for example clean water. Alternatively, the sample inlet can temporarily be closed. This leads to diluent alone flowing through the apparatus to the measurement zone.

Further, if the apparatus blocks, or where cleaning of the sample inlet is required, a simple back flush of the apparatus is possible. By restricting or closing the fluid outlet from the apparatus while diluent only is passing through the probe, all diluent will be expelled through the sample inlet.

In a particularly preferred embodiment, the apparatus of the present invention is intimately coupled to, or formed integrally with, the particle size distribution analysis measuring apparatus, for example a laser diffractometer. In this preferred embodiment, the entire diffraction system could be mounted on the apparatus. This dramatically shortens the path length between sampling and measurement of the sample, and tightly integrates the apparatus and the optics. In such a configuration, the optics are dedicated to the sampler configuration, consequently, there is no need for cell interchangeability. The optics may be relatively simple and the alignment fixed. In this configuration, the measurement cell may be split to simplify cleaning, for example, by using a form of fast lock fitting. Such a system may additionally comprise operating software and display means in order that results may be observed by the user.

In a further and preferred embodiment of the present invention, an auto-sampling system is provided. The apparatus of the present invention can be used to entrain sample from a plurality of sources, for example a tray containing a plurality of individual samples. The samples may be provided in a dilute slurry, concentrated slurry or dry powder form. In order to entrain a concentrated slurry or a dry powder, some dilution of sample is required. In this case, the fluid outlet of the apparatus may be temporarily closed or blocked in order to eject diluent from the sample inlet into a predetermined sample. Subsequently, either by manual operation or under the control of a computer, the fluid outlet may be opened, thus leading to the entrainment of sample and subsequent measurement. Between each sample, a background reading may be taken simply by closing the sample inlet, thus causing through flow of diluent alone. The closure of the sample inlet may then be removed and entrainment of sample and subsequent measurement proceeds. A plurality of such operations may occur, leading to rapid processing of a number of samples from different sources. Separate sample handling may be eliminated, thus increasing the efficiency of the processing. The whole auto-sampling process may be operated entirely or in part under the control of a computer processor.

In a further preferred embodiment of the present invention, a probe described herein may be linked to a process stream such that regular or continuous sample measurements may be taken from the stream. Thus, a probe may be coupled to a means to insert and withdraw at least the sample inlet into a process stream, for example a conduit or pipe, containing sample. Preferably, insertion/withdrawal means is automatically controlled, preferably under the control of a computer processor. Means are preferably provided to enable sequential sampling and cleaning of the device as it is respectively inserted and withdrawn from the process stream.

In a further embodiment of the present invention, there is provided a dilution apparatus in accordance with the present invention, wherein the apparatus is formed in a substrate, for example a cast or milled plate or monolith. Preferably, the mixing conduit has a substantially rectangular cross section. Furthermore, any of the sample inlet, the housing, and the throat section may have a rectangular cross section. This embodiment is particularly preferred when the features of the present invention are milled or otherwise formed in a plate or monolith. For example, a milled rectangular section version of the dilutor in which all of the internal cavities are formed by milling into a plate may be produced. The configurations of the features of the invention may be machined out in one or more operations. In a particularly preferred embodiment, a plurality of inter-linked channels are milled into a plate. The configurations of the channels form one of more of the features recited in the statement of invention. The apparatus may have a plurality of dilution stages, for example, 2, 3, 4, 5 or 6 stages. The apparatus may be constructed from metal or plastic. This embodiment is preferred for a disposable or low cost continuous sampler because it can be readily manufactured using a single CNC milling & drilling programme, or be moulded in plastic. This device preferably includes a fixed number of dilutions and multiple outlets each carrying the diluted stream from a single probe. The user preferably pumps dispersant into the entire probe and connects the appropriate outlet to the instrument. In this embodiment, the introducer tip is preferably an entry port. The position of this and the section thereof are preferably optimised to maximise the pressure drop and entrainment rate.

In a further embodiment of the present invention, the output from one dilutor may be blended with the output from another dilutor in order to create intermediate dilution ratios. One benefit of blending stages is to simply add the two outputs from dilutor n and n+1 in full. If it is assumed, for example, that a single probe dilution is 10:1 then the main effect of the blending is to double the diluent content whilst leaving the total sample consumed constant. So long as there is care to homogenise this mixing the net result is an apparent dilution ratio of 5:1. It is a small further step to consider that the blending of fractions of these outflows can give any intermediate dilution so long as the sample is properly homegenised afterwards.

DETAILED DESCRIPTION OF THE INVENTION

Figure 1:
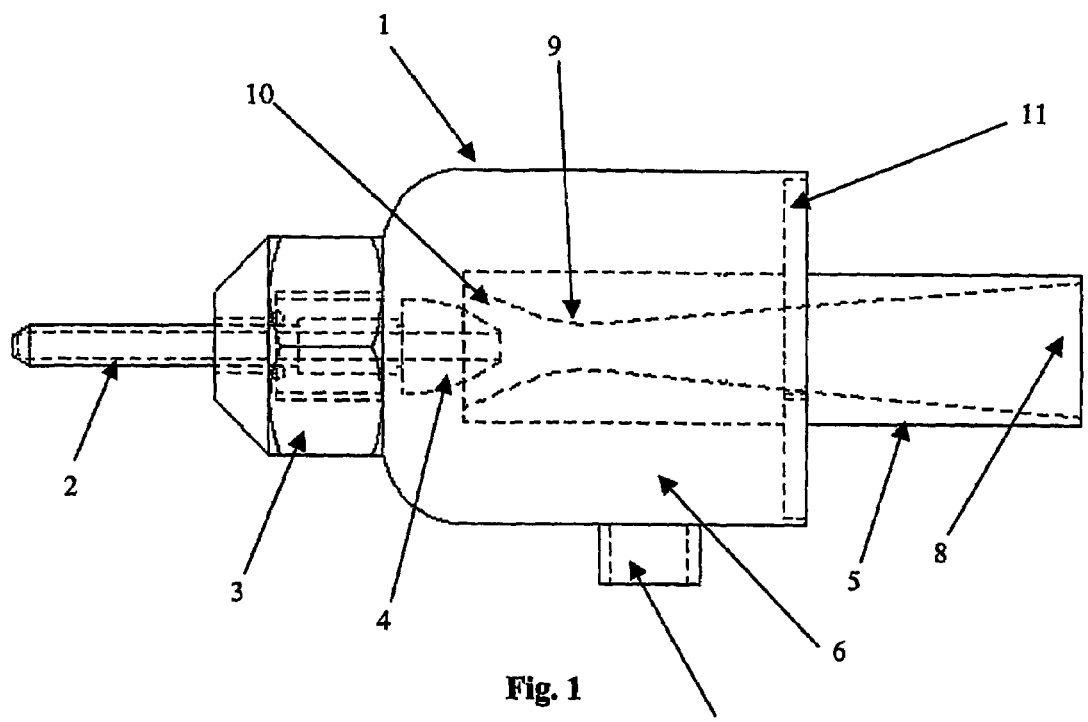
FIG. 1 shows a side view of a single dilution apparatus.

A sampler probe A has a cylindrical housing 1, typically having an internal diameter of 10 mm and a cavity length of 50 mm. The housing is connected to a sample inlet 2 at one end of the housing, in this case a thin walled stainless steel fine tube, typically having an internal diameter of 1.5 mm. The sample inlet has an introducer tip 4 that has a head section which tapers down to the point at which sample is discharged into the housing. It can be seen that the shape of the introducer and the mouth are broadly complementary in shape. Their detailed shapes are optimised to maximise the pressure drop experienced at the introducer tip during operation. The sample inlet 2 is connected by a collet lock 3 allowing minor adjustments to be made in the positioning of the tip 4 of the sample inlet 2. The mixing conduit 5 is connected to the housing 1 and sealed such that diluent entering the cavity 6 through the diluent inlet 7 can only pass out of the sampler via the sample inlet tube 2 or the fluid outlet 8. The mixing conduit has a throat section 9 having a diameter of 3 mm and a mouth portion 10 having a widest diameter of 8 mm, into which the sample introducer tip 4 is partially inserted. The mouth portion 10 tapers down to the throat portion 9, the throat portion being succeeded by a divergent portion of tube which proceeds to the fluid outlet 8.

Figure 2:
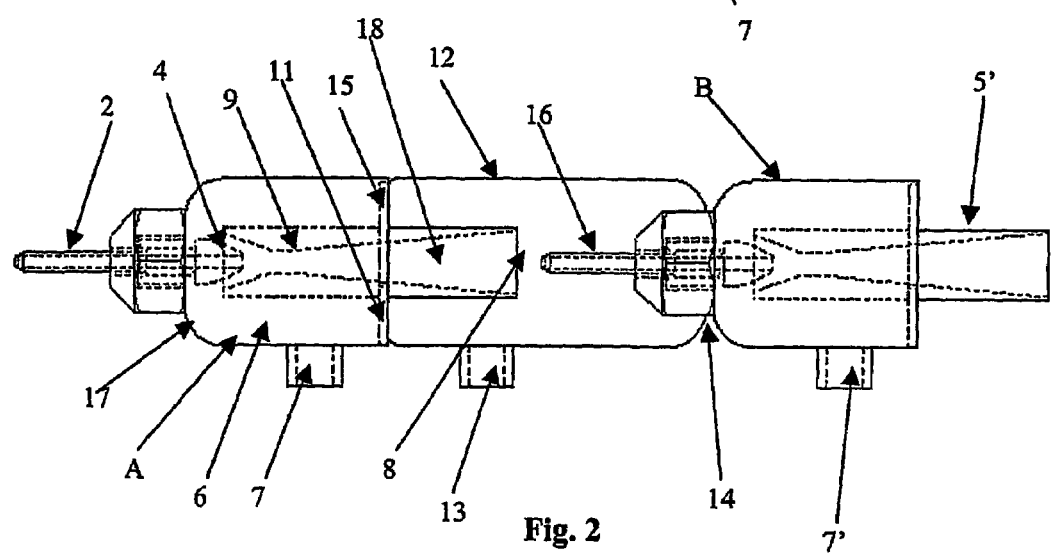
FIG. 2 shows a side view of a series of two dilution apparatus.

FIG. 2 shows a stack of 2 probes, A and B, connected to one another by a bridge piece. The end piece of the housing 11 is connected to a bridge piece 12 into which the fluid outlet 8 from probe A protrudes. The bridge piece 12 has a fluid outlet 13 and means for connecting to a second probe B. The bridge piece is connected by a screw fitting 14 at the end attached to probe B. The end of the bridge piece attached to probe A is connected by a screw thread 15. This allows the position of the fluid outlet 8 to be adjusted with respect to the outer tip of sample inlet 16 of probe B. Probe B is substantially of the same construction as Probe A. It should be understood that a series of such probes may be attached to one another to provide a series of cascaded, dilution apparatus. With reference to FIG. 2, diluent enters through diluent inlet 7 and flows up the cavity 6 within the housing 1 until it reaches the end point 17. The diluent then reverses direction and moves past the sample introducer tip 4, into the mouth of the mixing tube 10 and past the throat section 9. Due to the venturi effect, a pressure drop is experienced in zone 18 and causes sample to be drawn down the sample inlet tube 2 and entrained in the diluent. Diluent and entrained sample continue to flow down the mixing tube 5 and into the bridge portion 12. Strong turbulent mixing in this zone causes the entrained sample to be homogenously dispersed into the diluent. Some of the diluent and entrained sample are diverted through fluid outlet 13 while some diluent and entrained sample enter the sample inlet tube of the second probe B. Diluent and entrained sample flow into the second probe B and are in turn diluted by diluent from inlet 7'. As with probe A, diluent moves into the mixing tube 5' and entrains diluent and entrained sample from probe A.

At high sample concentrations it is possible that the sample inlet 16 can block with sample, this is most likely to occur at the first probe of a series due to the fact that the sample concentration is highest at this point. Such a blockage can result in a null signal from a particle size detector. In response to such a null signal the final outlet from the series of probes, (or any outlet) can be closed in order to build up a back pressure and blow the blockage from the inlet 16. A control system is typically employed to control diluent flow about the series of probes and may periodically execute a maintenance step of cleaning sample inlets by closing the fluid outlet 8 of the final probes in the series in order to blow and particles from probe inlets.

When sufficient dilution is achieved, diluent and entrained sample exiting from the last probe in the series can be taken directly to the particle analysis zone. Such a series of probes can form a permanent in-line dilution system for use in particle analysis is a manufacturing environment, for example in the production of Titanium Dioxide based pigments or it can form part of a portable particle analysis system.

Figure 3:
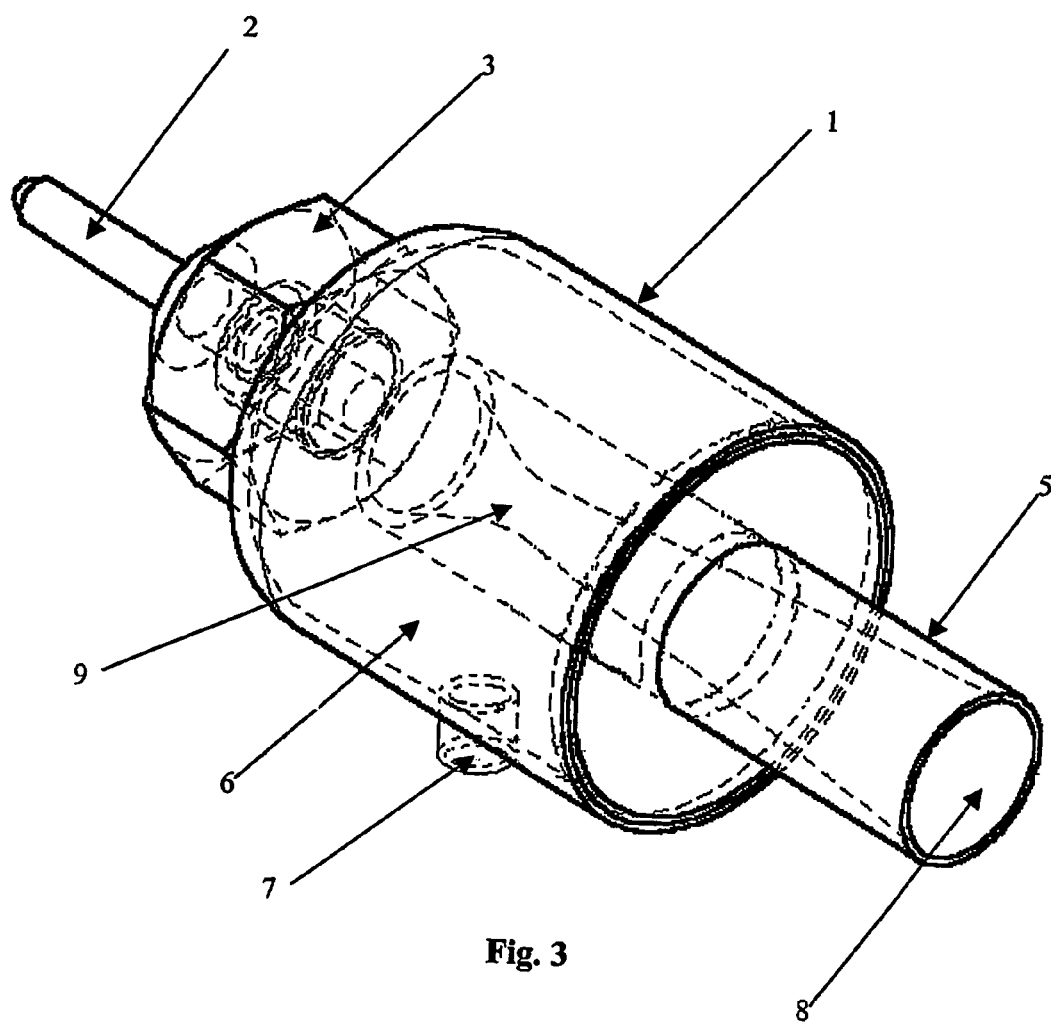
FIG. 3 shows a perspective view of the single dilution apparatus of FIG. 1.
Figure 4:
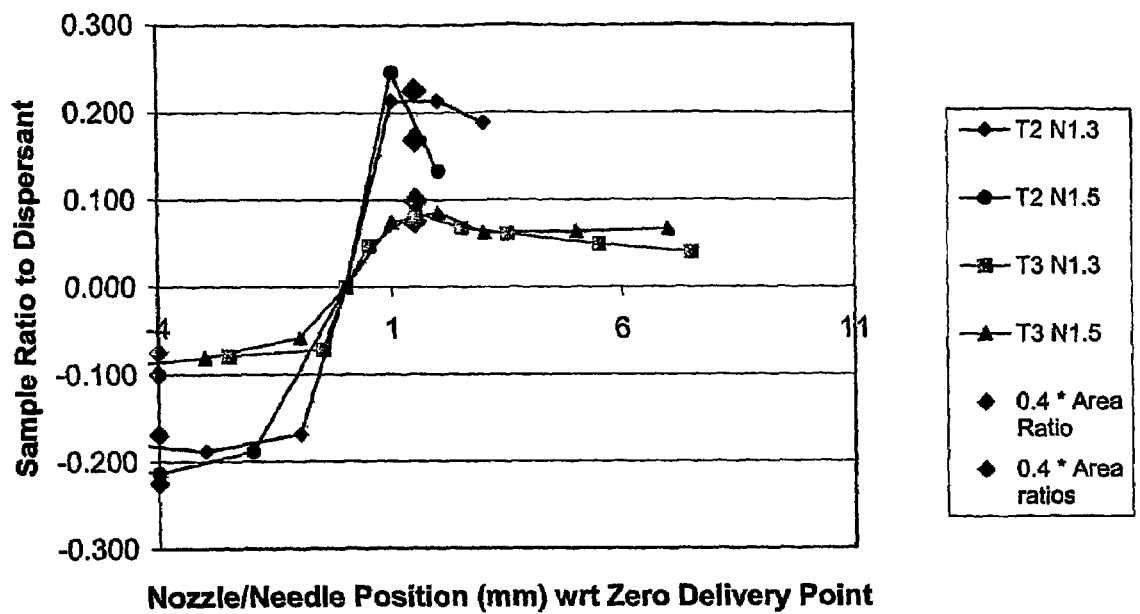
FIG. 4 shows calculated flow rates for a range of dilution apparatus dimensional settings.
Figure 5:
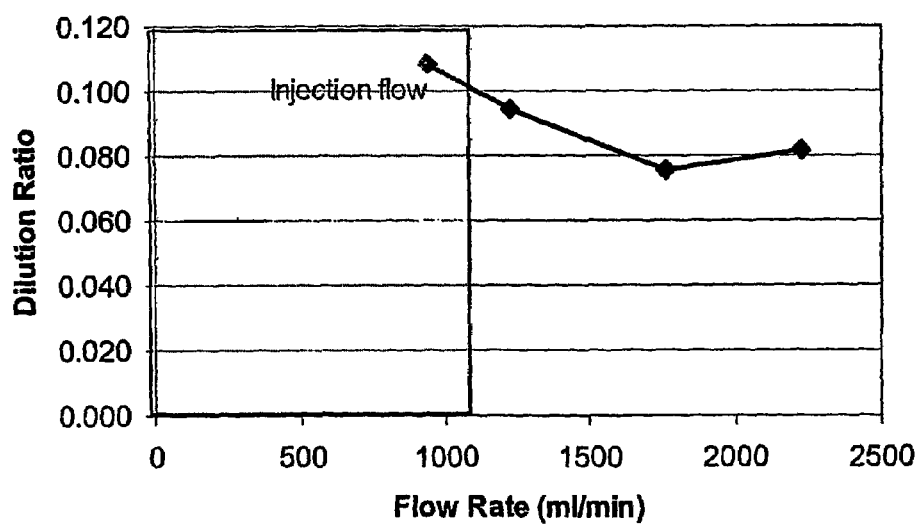
FIG. 5 shows a dilution ratio plot for a dilution apparatus having a 3 mm diameter throat and a 1.5 mm diameter sample inlet tube.

FIG. 3 shows a perspective view of a single probe.

EXAMPLE 1

Initial Assembly and Test of Dilution Apparatus.

The dilution apparatus probe described above was assembled to a Malvern Mastersizer MS 2000 particle size distribution analyser and fed from a normal domestic tap. The probe was set to run at a flow rate of approximately 1.9 litres/min of water.

With the sample inlet tube fully out of the throat the sample inlet tube sprayed water out. As the mixing tube inlet was lowered over the sample inlet tube the flow rate slowed, stopped and then started drawing air into the flow. As the mouth was further pushed over the sample inlet tube the rate of bubbling steadily increased showing the probe increases in efficiency until at a peak setting the air injection was a maximum.

Figure 6:
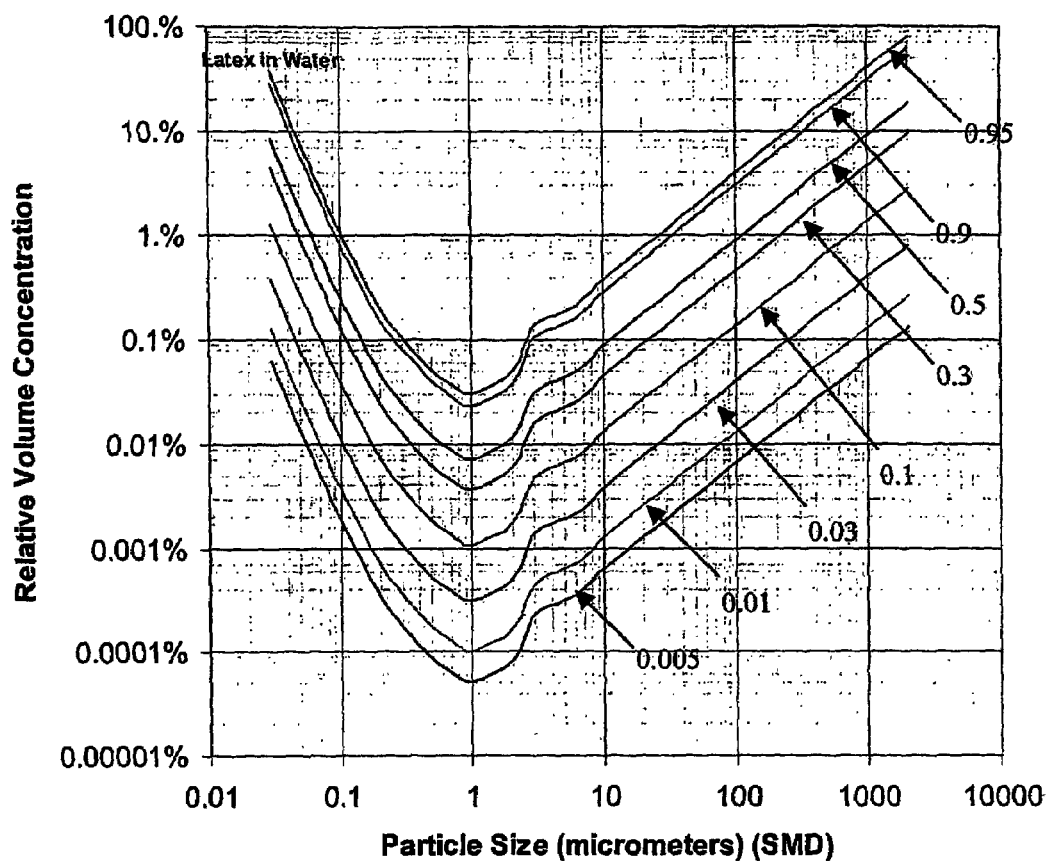
FIG. 6 shows an obscuration isobar plot for a 2.5 mm cell.

Bubbles were clearly visible in the diluent output of the probe and changing the separation of the mouth and the sample inlet tube changes the number of, and size of them. If a seal is placed over the sample inlet tube the bubbling stops and the system flows clean water. This is a useful condition for making a background measurement. The fact that this clean stream was bubble free was established by connecting to the MS 2000 and performing an alignment and background measurement. The presence of bubbles in the dispersant would be observed in background measurements as a dynamic scattering signal. No such signal evidence could be obtained. One benefit of the continuous sampler was apparent in that, once the flow had settled, and the cell temperature had equilibriated to the input stream, the backgrounds on the flowing diluent were as stable as that achieved for an analyser with no cell fitted. This highly desirable result means that measurements made in continuous dilution on-line have the potential to be as sensitive to size changes as a laboratory system, or marginally better.

When the sample inlet tube in this condition was dipped into clean water to simulate a sample stream the system consumed the sample. The system remained bubble free indicating that the mode of operation of the sample inlet tube had not altered in switching from air to water as the entrained sample.

A volume test was performed to assess the condition and it was established that the dispersant flow rate of 1.8 ltrs/min drew sample liquor at the rate of 136 ml/min, a dilution rate of approximately 14:1. The probe was adjusted over the range and the test re-performed to establish what range of dilution ratios could be achieved. With the 1.81 ltrs/min flow rate the dilution ratio could be easily varied from 20:1 to 6.8:1, dependent upon the design of the probe head, typically this design is not varied during use. Intermediate sample. dilutions can be achieved by blending a mixture of outputs from different probes in the series, e.g. the $n^{th}$ and the $n+1^{th}$ probes. For example mixing equal volumes of 10:1 and 20:1 dilutions ratio liquor results in a 15:1 dilution ratio liquorIn order to test the mixing of the sample, a measurement situation was set up with a benign and stable material. Intralipid solution was used as sample in a 3% volume concentration and this used as a stock material into which the sample inlet tube was dipped.

On running the probe at the 14:1 dilution position that represented the mid-range of capability it was discovered that the obscuration generated was 95% on the MS 2000. The sample was instantly dispersed and flowed through the cell giving completely stable outer ring scatter from the diluted Intralipid. It is evident that the sample inlet tube and expansion zone provides all the necessary mixing needed to fully disperse the material.

During background measurements the sample inlet tube was stopped using a bung. The rubber of the bung blocked the probe so that on release the system did not entrain air or sample. This gave an opportunity to test the probe blockage clearance. The outflow from the diluent outlet was temporarily restricted, and the water pressure then ejected the blockage from the sample inlet tube. As soon as the water outflow was resumed the sample inlet tube returned to sucking air or sample.

EXAMPLE 2

Three variants of the single probe described above were produced with different sample inlet tube and mixing tube dimensions. The throat of the mixing tube was machined to be 2 mm and 3 mm in diameter in Tubes T2 and T3 respectively. The sample inlet tubes were manufactured from stock stainless tubes and had 1.5 mm and 1.3 mm diameters. These are referred to as N1.3 and N1.5. All mixing tube and sample inlet tube configurations were exemplified.

The experiment performed initially worked with a constant head of dispersant water and variation of the geometry of the tube and sample inlet tube to locate the operating range. Measurements were made using a reference position on the probe. During the traversal of the mixing tube over the sample inlet tube the sample inlet tube initially pushed liquid out of the sample inlet tube and then at some point went to a zero flow condition. Further sample inlet tube movement resulted in suction. This zero point for flow was taken as the fixed point for referencing sample inlet tube dimensions as it was easy to experimentally locate.

The amount of liquid sucked (positive) or blown (negative) was recorded by measuring the time taken to suck or expel 100 ml's of water. The flow rate of dispersant was recorded by measuring the time taken to fill a 1 litre flask. From these figures the flow rates per minute were established and the dilution ratio of sample stream identified. The values for each sample inlet tube and mixing tube combination are shown in FIG. 4. The plots in FIG. 4 characterise the dilution ratio over the whole of the useful range of positioning of the components.

Once the mixing tube began to suck, the efficiency of entrainment rapidly reached a peak value after which further extension of the mixing tube caused a drop in dilution ratio again.

It was noted that at the peak point for entrainment, when the ratio was a maximum the dilution ratios were very similar to those for the fully withdrawn probe, based purely on matching cross sections. The same empirical efficiency ratio was also involved of 0.4. It suggests that at the maximum efficiency point the sample inlet tube is entraining liquid at the same velocity as is passing in the mixing tube and the dilution becomes set purely by the relative cross sections. The factors influencing the 0.4 ratio are clearly related to the differential pressures experienced in each outlet from the probe.

EXAMPLE 3

A favourable condition for further testing the probe was taken to be the T3 mixing tube and the N1.5 sample inlet tube as it gave the highest stable dilution ratio in the tests. For this condition a fixed separation of sample inlet tube introducer surface to mouth surface was set at +2 mm and a series of dilution ratio checks were performed at a range of flow rates. The results are charted in FIG. 5. The injection ratio is quite constant so that the rate of consumption of slurry is set by the dispersant consumption.

The dispersant flow rate has a minimum condition to establish a reliable head. The system could be run at the lowest flow rate that achieves reliable dilution since otherwise the system is simply consuming sample and dispersant unnecessarily. An alternative is to run the system at the maximum entrainment setting.

In order to explore the utility of the continuous dilutor it was decided to compute the obscuration isobars for a typical laser diffraction system. For a 2.5 mm cell, as fitted to the Mastersizer 2000 the volume concentrations were predicted for a scale of constant obscurations. The plots were made for the case of Latex in Water and will differ in fine detail for different material and dispersant properties. In essential details however the behaviour is similar for all materials, bearing in mind the log-log nature of the plotting. The obscuration isobars were plotted for cases from 0.005 representing the limit of detectability for Mastersizer 2000, to 0.95 the upper limit for multiple scattering correction in the Malvern Insitec, a sister product to the Mastersizer 2000. Useful values in between were included simply to help locate "favourite" values typically used as targets for dilution. The basic plot is shown in FIG. 6. It makes clear the strong particle size relationship that links volume concentration and obscuration of the laser. The plot is computed using Beer Lambert Law and Mie Theory. In fact practical experience with laser diffraction shows that the onset of multiple scattering does not occur at a fixed threshold based on obscuration. For sub-micron latices multiple scattering can be detected at obscurations of 5% where for larger materials it is apparently benign at 50% obscuration.

The plot is useful as a way to predict the obscuration condition that will be created by a given concentration of material. The Particle Size in the plot was for a narrow log-normal, essentially a delta function. However theory shows that for polydisperse materials the predictions are exactly correct if the Sauter Mean Diameter (SMD) of the particle distribution is used as the Particle Size.

Figure 7:
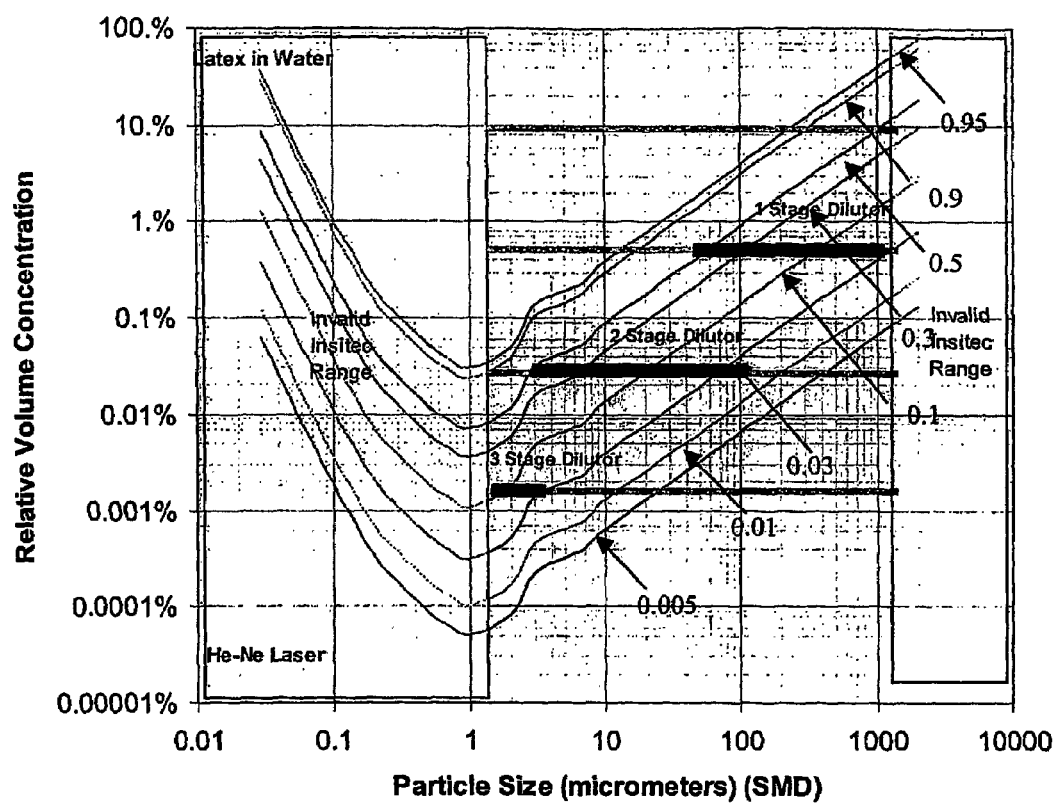
FIG. 7 shows an overlay of FIG. 6, with considerations for operating an Insitec particle size distribution analyser.

The way in which the plot shown in FIG. 6 can be used is illustrated in the plot shown in FIG. 7. Here the chart has been overlaid with the considerations for operating the Insitec product for 10% volume concentration slurries. The reduction in concentration for successively stacked dilutor stages is shown as a series of horizontal lines.

The thickened black part of each line shows the range over which the obscuration passes from 3% to 50%, a range that is arbitrarily considered to be the target concentration range to work within. What this shows is that the stacked dilutors overlap in capability terms so that other variable dilution stages could be ignored. In addition it is possible to use the 10:1 dilution ratio version of the dilutor and it would still need only 3 stages of dilution maximum and would have a more comfortable overlap region in concentration terms. It is worth pointing out that for more absorbing particles than latex the entire range would have been covered with only two stages of dilution maximum. Since they each can be run down to 1 ltr/min this offers a dispersant consumption of 2 ltr/min for absorbing materials and 3 ltr/min for fine transparent materials.

EXAMPLE 4

Three Stage Dilution

For convenience in testing three probes were matched with bridge pieces and labelled. The first probe in contact with the raw slurry was probe A, with B and C respectively further down the dilution chain. These labels and order of assembly were adhered to through all testing.

Defining Terms

In order to be more exact in the definition of properties of the dilutor chain the following terms are defined.

$C_0$ Initial slurry volume concentration before dilution $C_A$, $C_B$, etc Slurry concentration at the outflow of probe A, B, etc.

$I_A$, $I_B$, etc Dispersant flow rate at inlet of probe A, B, etc.

$O_A$, $O_B$, etc Mixed slurry flow rate out of probe A, B, etc.

$S_A$, $S_B$, etc slurry sampling rate into probe A, B, etc.

We define an Entrainment Ratio $\alpha$ $$\alpha_A = S_A/I_A$$

Using this the output and input concentrations are related by $$C_A = C_0 \cdot [\alpha_A/(1+\alpha_A)]$$

The term $[\alpha_A/(1+\alpha_A)]$ will be referred to as the "Dilution Factor" and its reciprocal the "Dilution Ratio".

So for a chain of 3 dilutors A, B, C $$C_C = C_0 \ldots [\alpha_A/(1+\alpha_A)] \cdot [\alpha_B/(1+\alpha_B)] \cdot [\alpha_C/(1+\alpha_C)]$$

To consider the effects of any size dependant bias in the dilution of the probe we can introduce the bias factor $\beta(a)$, where a represents the particle size. $\beta(a)$ is defined as the ratio of the relative volume of the size a in the output size distribution to the ration of the relative volume of the same size in the input size distribution. This factor is 1 when there is no bias in the dilutor at size (a) and will be greater than 1 if the size (a) is over-represented by volume in the output stream, and less than 1 if under-represented. The bias then makes the output concentration a size dependent effect as below $$C_A(a) = C_0 \cdot \beta(a) \cdot [\alpha_A/(1+\alpha_A)]$$

In practice when a series of probes are coupled together the dilution ratios become interacting due to the variation in the inlet and outlet pressures caused by the coupling. The dilution ratios can be measured by careful measurements of the flow rates of the inlet and outlets, the various S values being obtained by subtraction.

For a dilutor operating close to its maximum entrainment efficiency the effect of inlet and outlet pressure variation is minimal and to a first approximation the dilutors could be considered to be identical so that $\alpha_A = \alpha_B$ and so on, and can be replaced by the single $\alpha$. The same applies to inlet, outlet and slurry concentrations.

Then, for an n stage dilutor:

$$C_n(a) = \alpha^n \cdot \beta^n(a)/(1+\alpha)^n$$

Total consumption rate of diluent $I_{tot}$ $$I_{tot} = n \cdot I$$

Total consumption rate of initial slurry is $S_{tot}$ $$S_{tot} = \alpha \cdot I$$

These are useful guidance rules for establishing the impact of a multi-stage dilution. As the number of stages is increased the rate of consumption of slurry is fixed, the consumption of diluent goes up in proportion to n and the dilution ratio increases by the $n^{th}$ power. The impact of any size dependent bias increases by the $n^{th}$ power too however, emphasising the importance of careful optimisation. Thus, large dilutions can be readily achieved for a small number of dilutor stages employed, this is important in reducing multiple scattering and other deleterious concentration related effects from particle characteristic measurements.

Dilution Ratio Tests

It was decided that each probe needed to work at its maximum entrainment efficiency even though this meant that the dilution ratio was at its lowest. The reason for this is that the probe is at its most robust in this condition and least affected by variations in its environment. Each probe was set up individually by adjusting them at the full available water pressure. The mixing tube position was adjusted to achieve the maximum bubble formation in the exit pipes and then locked. The rates of liquid consumption were monitored and the dilution ratios of each individual probe were as below in Table 1:

TABLE 1

| Probe | Dilution Rate (Dilution Ratio) |
|---|---|
| A | 0.11 (9:1) |
| B | 0.13 (7.7:1) |
| C | 0.14 (7.2:1) |

These values were achieved when each single probe was running with 3.3 ltrs/min of dispersant. The average consumption of slurry in this condition was 0.38 ltrs/min.

The unit was then assembled to form a 3 stage probe and the flow rates monitored. The available flow rate of 3.3 ltrs/min is now shared between each stage in a manner that is not entirely independent.

For the 3 stages the performance was as below in Table 2.

TABLE 2

| Probe | Flow Rate |
|---|---|
| A | 1.11 ltr/min |
| B | 0.97 ltr/min |
| C | 1.25 ltr/min |
| Slurry | 0.095 ltr/min |

The slurry consumption at the first stage is the only dilution ratio that can be extracted from this data since the subsequent stages sampling is not known until the exit sample concentrations are measured. The first stage dilution rate is 0.086 or an 11.6:1 dilution ratio.

Sample Testing

Intralipid

Figure 8:
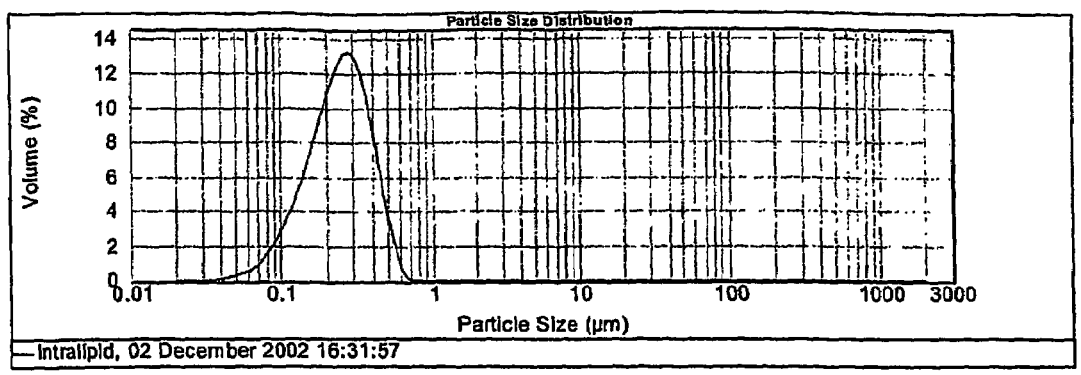
FIG. 8 shows the particle size distribution analysis of an intralipid solution.

Stock Intralipid solution was sampled direct from a 10% solution by volume. The 3 stage probe was used as assembled and the resulting dilution gave an obscuration of around 4%. The data and result collected for the Intralipid is shown in FIG. 8.

As should be apparent the inner ring signals were completely clear and the result is typical of that for Intralipid. The signals were completely stable and no data fluctuations were seen to indicate any lack of mixing or pulsatile operation. The Intralipid sample was clearly successful, however it represents a benign material in dispersion terms since it is so small that the particles will follow the flow and the mixing will simply track that of the fluid.

Fine Carborundum

A dense fine powder (Silicon Carbide, grade F600) was used in an analogous test to that immediately above. This has a particle size of around 10 μm and a quoted density of 3.2.

A slurry was made up of 30 g of SiC in 200 ml of water which corresponded to a 4.6% vol/vol mixture. The triple stage probe was immediately able to disperse this slurry to an obscuration of around 4.8%, near ideal for measurement.

Figure 9:
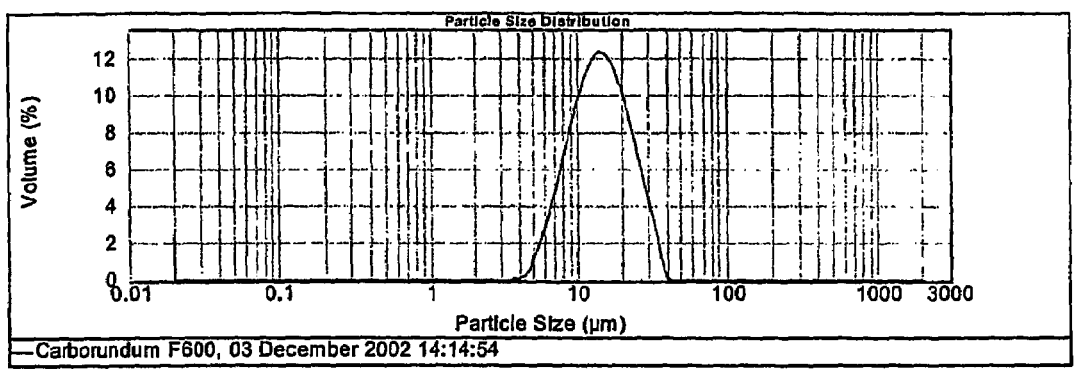
FIG. 9 shows the particle size distribution analysis of silicon carbide suspension.

The data and results for the carborundum are indicated in FIG. 9.

The mean size and width of the distribution above was compared to those obtained on a recent lab measurement of the same material. It should be clear that there are no distinguishable differences.

|  | Lab | Dilutor |
|---|---|---|
| Dv50 | 14.29 | 14.286 |
| Span | 1.267 | 1.261 |

Sample E

Figure 10:
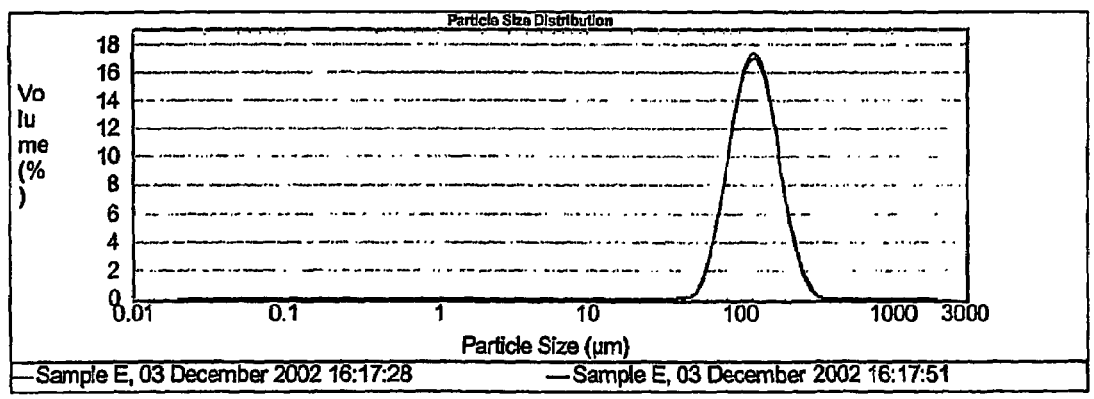
FIG. 10 shows the particle size distribution analysis of sample E.

A sample of larger particle sized material was also measured. The sample referenced Sample E was raw process slurry from a real application to produce a flame retardant and cannot be identified. The sample had particles of circa 100 μm, a density of <2 and this slurry was sampled raw through the triple stage probe. The results are shown in FIG. 10.

The obscuration for these measurements was an astonishingly low 0.82% and yet data quality was excellent giving testament to background stability that had been achieved after an extended period of running. This demonstrated the benefit of increased stability predicted for the probe system once temperature equilibriated with the dispersant. Note there are two consecutive measurements of the same sample in the same condition taken after removal and re-inserting the probe.

Figure 11:
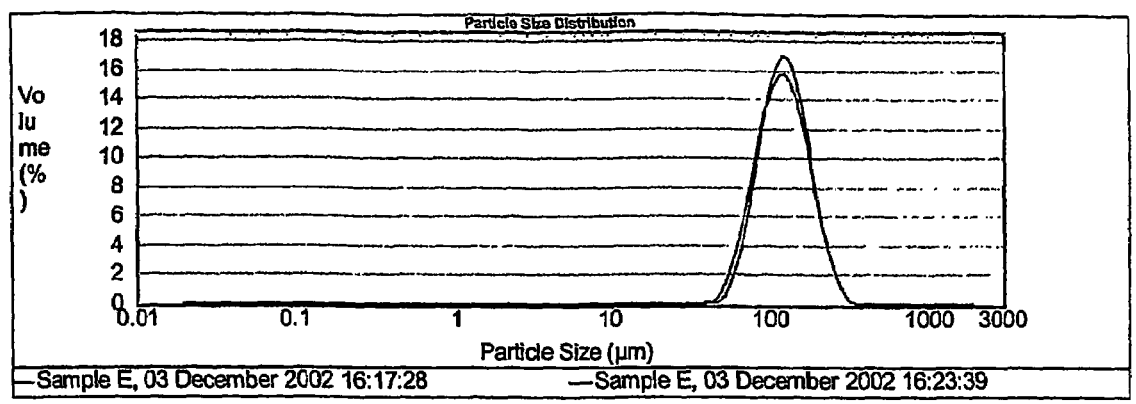
FIG. 11 shows a two-stage dilution particle size distribution analysis of Sample E suspension.

It was decided to operate the dilutor as a 2-stage probe instead and this gave the obscuration as 6.2% and a correspondingly larger signal energy. The results were near identical and the two results for 3 and 2 stages are shown overplotted in FIG. 11.

The differences between the results at the 2 dilutions were 2.8% on the mean size and 0.7% on the width. This was considered acceptable agreement given the low concentration of the 3-stage measurement.

EXAMPLE 4

Figure 12:
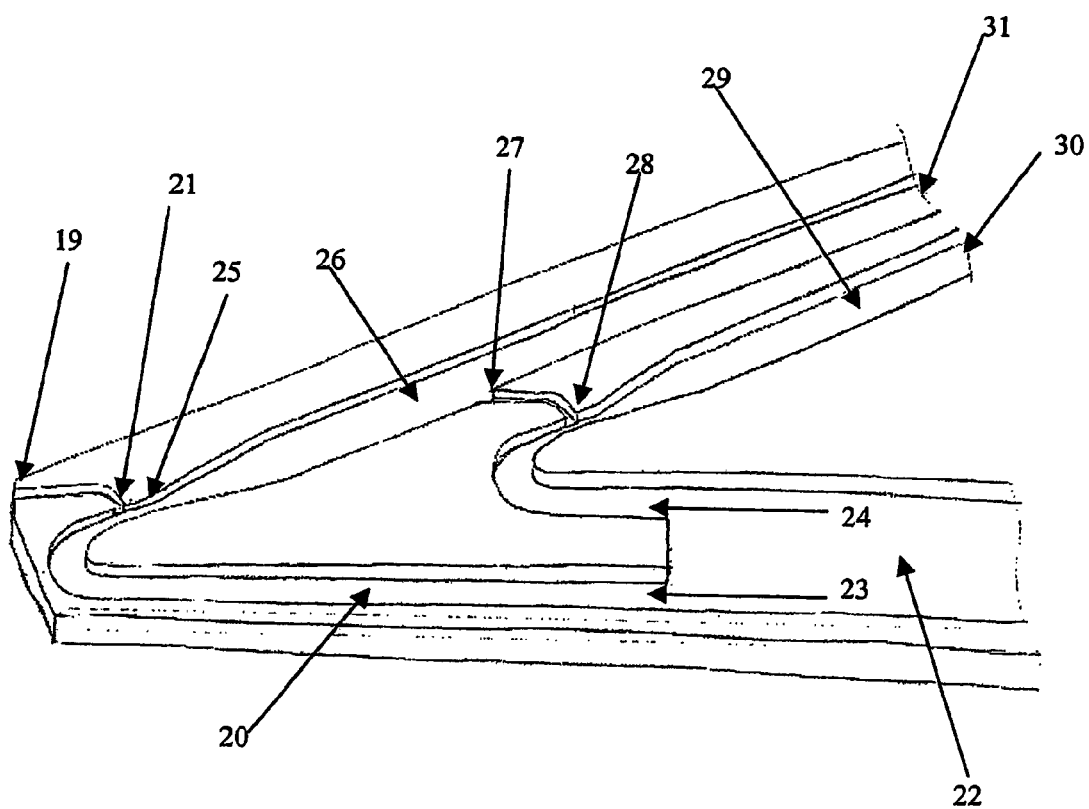
FIG. 12 shows section of a milled plate, into which features of the apparatus are machined.

FIG. 12 shows section of a milled rectangular section version of the dilutor in which all of the internal cavities are formed by CNC milling into a plate. The figure shows a two-stage dilution apparatus. The top of the apparatus which is required to provide a closed apparatus is not shown. The mill programme very accurately allows reproducible configurations to be machined out in one operation. A sample inlet 19 opens into the milled housing 20 at introducer point 21. Main diluent inlet 22 feeds both diluent inlet 23 for a first dilution stage and diluent inlet 24 for a second dilution stage. Diluent flows past introducer 21 and into the throat 25. Diluent then moves into the pressure drop region 26 and some diluent and entrained sample is drawn into sample inlet 27, passes through introducer 28 and moves down pressure drop section 29. Diluent may be removed through fluid outlet 30 and 31. This allows the external porting of the excess part-diluted slurry to a common single outlet for disposal. The plate has a flat top screwed on it to close the ports to the outside world. The apparatus is preferably constructed from metal or plastic.

Figure 13:
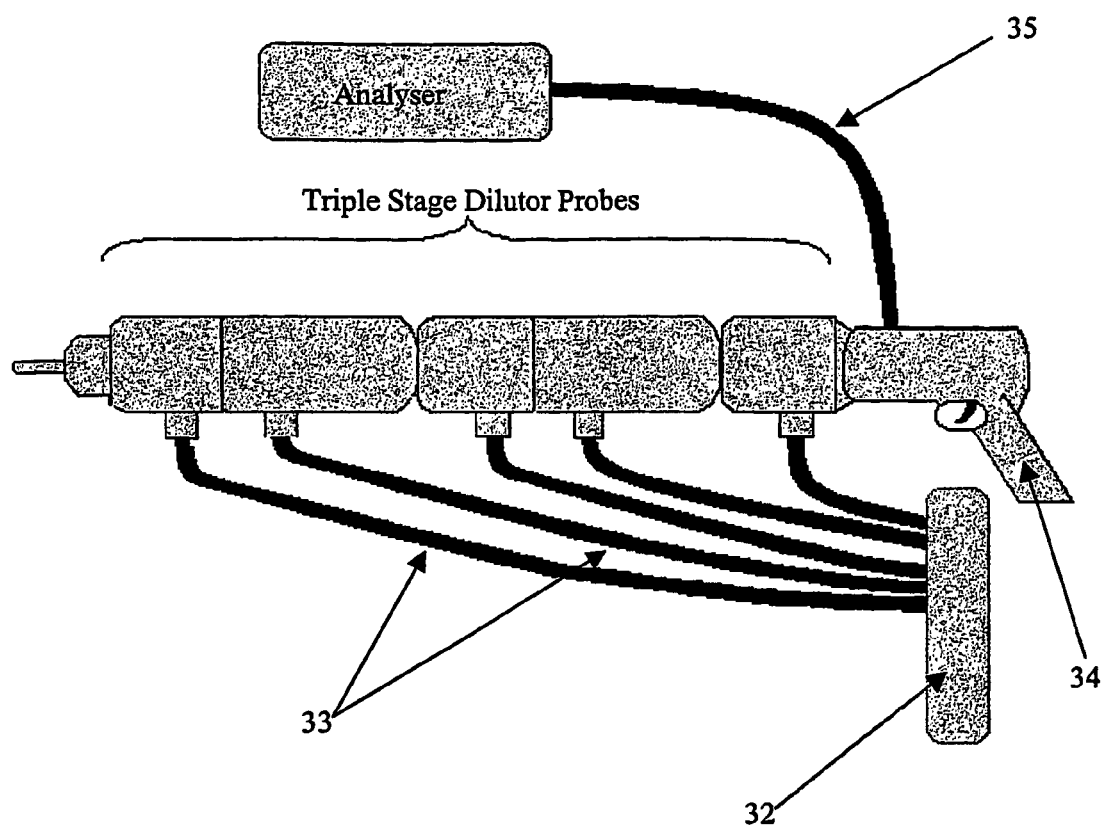
FIG. 13 shows a series of dilutor probes attached to a hand held actuator gun.

FIG. 13 shows a triple dilutor probe. The probe is attached to a diluent source 32, via a number of diluent hoses 33 (only two of which are indicated with arrows). The device is provided with a hand holdable grip 34. The grip is supplied with a trigger for actuating the device by initiating diluent flow. This may be effected by communication with the diluent source 32 to start pumping diluent into the device, or by actuating a valve within the device which allows diluent to start flowing through the device. The device is shown coupled to a particle characteristic analyser, in this case a particle size distribution analyser, by a hose 35. The hose 35 pumps sample-entrained diluent, having an appropriate dilution, into the analyser for analysis. Diluent and sample-entrained diluent may be fed back into the process from which the sample was obtained or may be otherwise disposed of.

Figure 14:
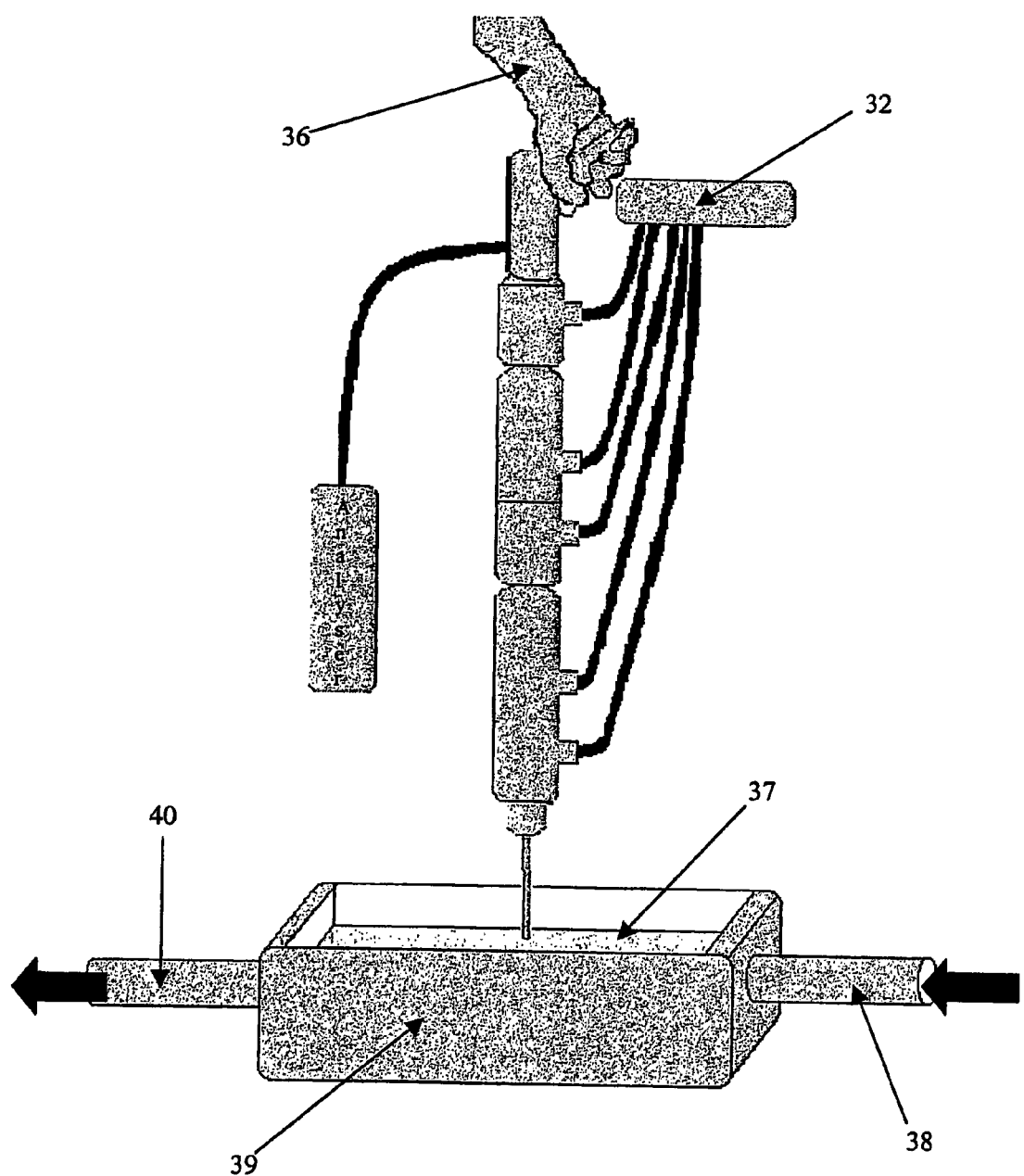
FIG. 14 shows the apparatus shown in FIG. 13 taking a sample from a process stream.

FIG. 14 shows the apparatus shown in FIG. 13 taking a sample from a process stream. The apparatus is shown being held by a hand 36. The apparatus is shown being dipped into a process sample stream 37. The stream is shown entering a sample conduit 38 in the right of the figure (indicated by a solid arrow) and entering a sample bath 39 from which it is particularly convenient to take sample. The sample is pumped through the bath and exits via a second conduit 40 (indicated by a solid arrow).

The sample is diluted and fed to an analyser very quickly. This allows for rapid and continuous monitoring of the process.

Figure 15:
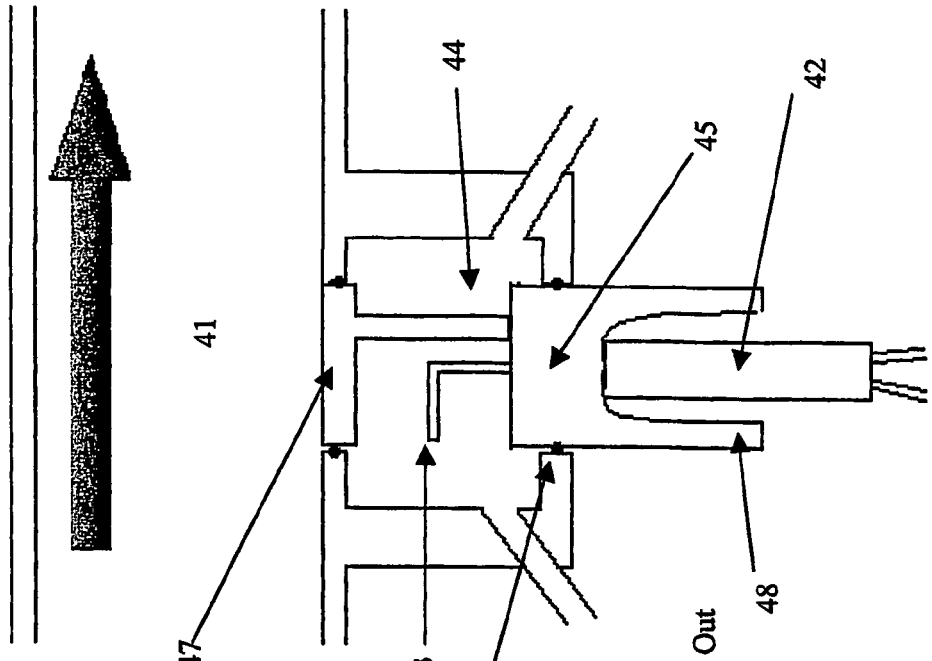
FIG. 15 shows an embodiment of the present invention, adapted to receive and dilute sample from a process stream.
Figure 15:
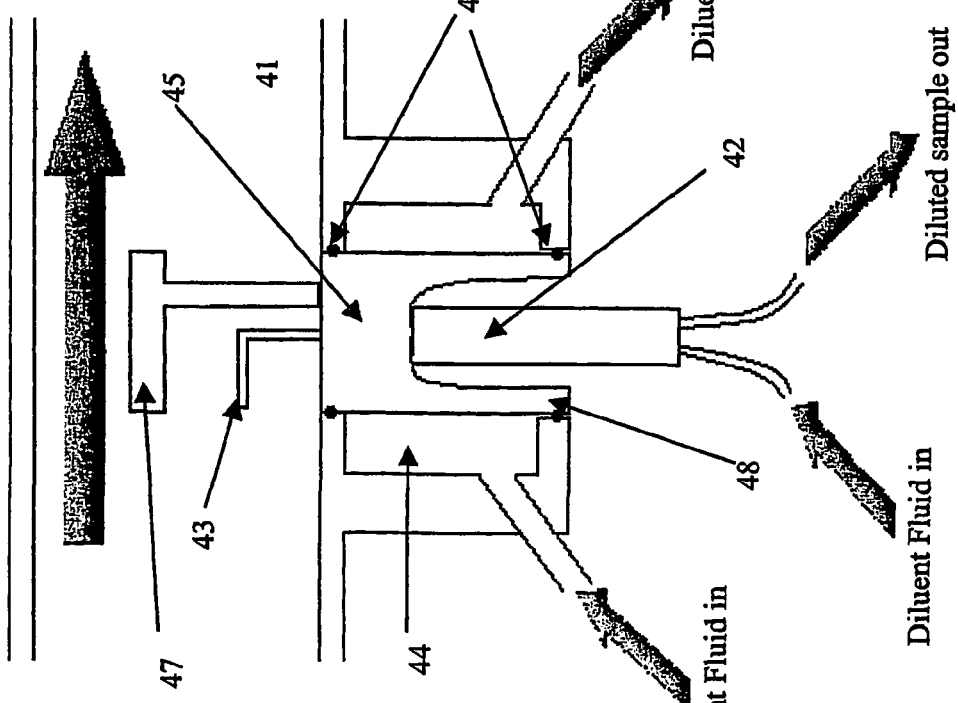

FIG. 15 shows an embodiment of the present invention, adapted to receive and dilute sample from a process stream 41, in this specific embodiment, a process pipe or conduit.

The probe is illustrated in two configurations: a sampling configuration shown on the left of the page, and a background configuration shown on the right.

In the sampling configuration, the probe 42, which may constitute a single or series of dilutors, as described herein, is exposed to the process stream to contact the sampling tip 43 with sample. In the background configuration, the probe is withdrawn from the sample stream and is housed in a cavity 44 that is optionally being continually refreshed with diluent. The probe end 45 has been extended to create a piston-like structure that may move between the two configurations. The piston 44 is preferably sealed, for example, by O-ring seals 46 designed to keep the process stream sealed in the pipe.

The sampling tip 43 is broadly equivalent in function to feature 2, described with reference to FIG. 2. The probe housing attached to sampling tip 43 is a single dilutor, or first in a series of dilutors, the tip preferably being adapted to facilitate uptake of sample from the process stream 41.

The piston is preferably circular in radial cross section. A sealing cap 47 is provided over the top of the sampling probe and is preferably shaped for sealing engagement with the pipe section, as shown in the background configuration. The supports that fix this plate are preferably downstream of the sampling probe so that their section does not affect sample flow around the probe.

The sampling inlet itself is preferably shaped so that the sample intake point of the sampling tip 43 faces the sample flow. This enables the possibility of isokinetic sampling by control of the relative geometry of the pipe and sampling probe sections.

In use the system is initially in the background configuration and withdrawn from the process stream. The probe(s) 42 may continually run diluent and so the sampling probe is entraining diluent from the cavity it is sitting in. This allows the system to remain clean during non-use and also allows background signals on the diluent only to be taken by the measurement apparatus where required. It may also be desirable to flush this cavity with a cleaning liquid rather that pure diluent. For example, in the case of calcium carbonate the cleaning of the sample tip 43 would be more effective if a dilute acid was used since this would dissolve any residual calcium carbonate coatings. The acid is so diluted by the time it reached the instrument that it has no effect on background measurements. For other samples other chemical cleaning approaches can be tried, surfactants or admixtures can be used to neutralise particle adhesion forces.

Once a background is measured tests can be performed on the quality of that background in order to ensure that the analyser instrument is ready for measurement, tests can be applied for system alignment, transducer or window cleanliness, and so on.

Subsequent to optional testing of the analyser instrument, the probe can be pushed forward into the process stream, ie., moved into the sampling configuration. The probe end 45 comprises a portion proximate its distal end 48 that seals the cleaning cavity when the device is in the sampling configuration. This allows cleaning liquid to continue to flow around the piston but otherwise not interfere with probe operation. As diluent is already flowing in the probe, the system begins to entrain sample and dilute it out to the instrument. It will continue to do this for as long as the diluent flow is maintained and the probe is extended into the pipe. The instrument has access to a continual representation of the process flow delayed only a few seconds due to its passage through the probe(s).

Once the instrument has monitored the process to completion, or in the case of continuous manufacture at a planned maintenance point, the probe is again withdrawn into the background configuration and allowed to clean. If the instrument fails any background tests it is then necessary to stop the diluent flow to the probe(s) and allow them to drain. The instrument cell can then be disassembled for cleaning. During this time the probe may remain in the background configuration with the probe keeping the process sealed.

The invention claimed is:

1. A multi-stage dilution device, comprising a first stage dilution apparatus, and a second stage dilution apparatus, each of the stage dilution apparatus comprising:
   (i) a housing having a diluent inlet;
   (ii) a sample inlet having a sample introducer within said housing adapted to introduce the sample at an introducer point within said housing; and,
   (iii) a mixing conduit mounted at least partially within said housing, said mixing conduit having an inlet section comprising a mouth, and a fluid outlet, and a throat section capable of producing a pressure drop within said mixing conduit, said pressure drop being sufficient to draw sample through said sample inlet;
said introducer point of said sample inlet being proximate said mixing conduit inlet; and wherein said fluid output of said first stage dilution apparatus is in communication with the sample inlet of the second stage dilution apparatus.

2. The device according to claim 1 wherein said mixing conduit inlet section of each stage is remote to said diluent inlet of that stage.

3. The device according to claim 1 wherein, for each of the first stage dilution apparatus and the second stage dilution apparatus, said sample inlet and said inlet section of the mixing conduit are located proximate an end of said housing remote from said diluent inlet of that stage.

4. The device according to claim 1 wherein, for each of the first stage dilution apparatus and the second stage dilution apparatus, said housing forms a jacket around at least a portion of said mixing conduit, creating an annular cavity between said housing and said mixing conduit.

5. The device according claim 1 wherein, for each said stage, said throat section is proximate said mixing conduit inlet of that stage.

6. The device according to claim 5, wherein said throat section and said mixing conduit inlet are connected by a frustoconical section.

7. The device according to claim 1 wherein said sample inlet is a substantially cylindrical tube having a sample introducer tip.

8. The device according to claim 7 wherein said sample inlet tube has a diameter in a range from 1.2-2 mm.

9. The device according to claim 7 wherein said sample inlet tube has a diameter in a range from 1.3-1.5 mm.

10. The device according to claim 7, wherein said sample inlet tube is substantially co-axial with said mixing conduit.

11. The device according to claim 7 wherein said sample inlet tube has a diameter in a range from 1-4 mm.

12. The device according to claim 1 wherein there is an introducer tip of said sample introducer, said tip having a complementary shape to said inlet portion of said mixing conduit, optimised to maximise a pressure drop experienced at said introducer tip.

13. The device according to claim 1 wherein a separation of an introducer tip of said sample introducer and a surface of said inlet portion of said mixing conduit is in a range from 0.5 mm-5 mm.

14. The device according to claim 1 wherein an introducer tip of a diluter stage sample introducer is adapted to be in direct contact with the diluent when said device is in use.

15. The device according to claim 1 wherein the position of an introducer tip of the sample introducer is adjustable relative to said mixing conduit.

16. The device according to claim 1 wherein said first and second dilution stage apparatus are coupled together via couplers provided at ends of said stages.

17. The device according to claim 1, provided with engagement means coupling the first stage dilution apparatus to the second stage dilution apparatus, said engagement means comprising a bridge section having a sheath, a cavity, and a fluid outlet.

18. The device according to claim 1 wherein said first and second dilution stage apparatus are co-axially aligned.

19. The device according to claim 1 wherein there are more than 2 and up to 10 dilution stage apparatus coupled together.

20. The device according to claim 1 wherein the device is adapted to be hand held.

21. The device according to claim 1 intimately coupled to, or formed integrally with, a particle characteristic measuring apparatus.

22. A dilution device according to claim 1 wherein said sample inlet is disposed substantially on the elongate axis of said mixing conduit.

23. A dilution device according to claim 1 wherein said mouth comprises a converging surface in the direction of fluid flow in use.

24. A dilution device according to claim 1 wherein said mouth is circularly symmetrical about the axis of said mixing conduit.

25. A dilution device according to claim 1 wherein said sample inlet introducer extends in the elongate direction at least to the entrance of said mouth.

26. A dilution device according to claim 25 wherein said sample inlet extends in to said mouth, and is recessed within said mouth.

27. A dilution device according to claim 1 wherein said sample inlet has a tapering extension surface which converges along an elongate length of said sample inlet, and wherein there is a diluent flow gap defined between said extension surface of said sample inlet and said mouth.

28. A dilution device according to claim 27 wherein said diluent flow gap is generally annular at a cross-section taken normal to said elongate axis, the tapering external surface of said inlet proximate said tapering interior surface of the mouth, being generally co-axial.

29. A dilution device according to claim 1, wherein for each of the first stage dilution apparatus and the second stage dilution apparatus, the arrangement is such that when the sample is prevented from flowing through said sample inlet, the diluent is capable of flowing through said mixing conduit.

30. A method of cleaning a dilution device that is in accordance with claim 1, comprising closing said outlet of at least one stage of the device whilst applying fluid pressure to that stage of said device via said diluent inlet of that stage, thus causing venting of fluid through said sample inlet of that stage.

31. The device according to claim 1 wherein a separation of an introducer tip of said sample introducer and a surface of said inlet portion of said mixing conduit is in a range from 0.75 mm-3 mm.

32. The device according to claim 1 wherein a separation of an introducer tip of said sample introducer and a surface of said inlet portion of said mixing conduit is in a range from 1 mm-2.5 mm.

* * * * *